United States Patent [19]

Runge

[11] 4,176,411
[45] Dec. 4, 1979

[54] CARDIAC ASSIST DEVICE EMPLOYING ELECTRICALLY STIMULATED ARTIFICIAL MUSCLE

[76] Inventor: Thomas M. Runge, 2501 Galewood Pl., Austin, Tex. 78703

[21] Appl. No.: 855,219

[22] Filed: Nov. 28, 1977

[51] Int. Cl.$^2$ ............................ A61F 1/24; A61M 1/03
[52] U.S. Cl. .......................................... 3/1.7; 128/1.3; 335/219; 335/230; 335/303; 417/412; 417/478; 3/1
[58] Field of Search .......................... 3/1.7, 1.4, 1.1, 1; 128/1 D, 1.3, 1.5; 335/219, 230, 303; 417/478, 412, 322

[56] References Cited

U.S. PATENT DOCUMENTS

| | | | |
|---|---|---|---|
| 2,532,876 | 12/1950 | Asche et al. | 3/1 X |
| 3,720,485 | 3/1973 | Holman | 3/1.7 X |
| 3,733,616 | 5/1973 | Willis | 3/1.7 |
| 4,014,318 | 3/1977 | Dockum et al. | 3/1.7 X |

*Primary Examiner*—Ronald L. Frinks
*Attorney, Agent, or Firm*—B. P. Fishburne, Jr.

[57] ABSTRACT

A left atrial to descending thoracic aorta shunt is encircled by an artificial muscle sheath consisting of a multiplicity of connected rod-like segments formed of an elastomer. Each segment contains a series of embedded electromagnets and surrounding dispersed fragments of magnetically attractable material. The electromagnets are energized across intact skin of a recipient of the device by state of the art induction means to cause contraction of the individual artificial muscle segments with resulting contraction of the muscle sheath to thereby squeeze cyclically a predetermined volume of blood through the flexible shunt which is equipped at opposite ends of the muscle sheath with check valves.

9 Claims, 7 Drawing Figures

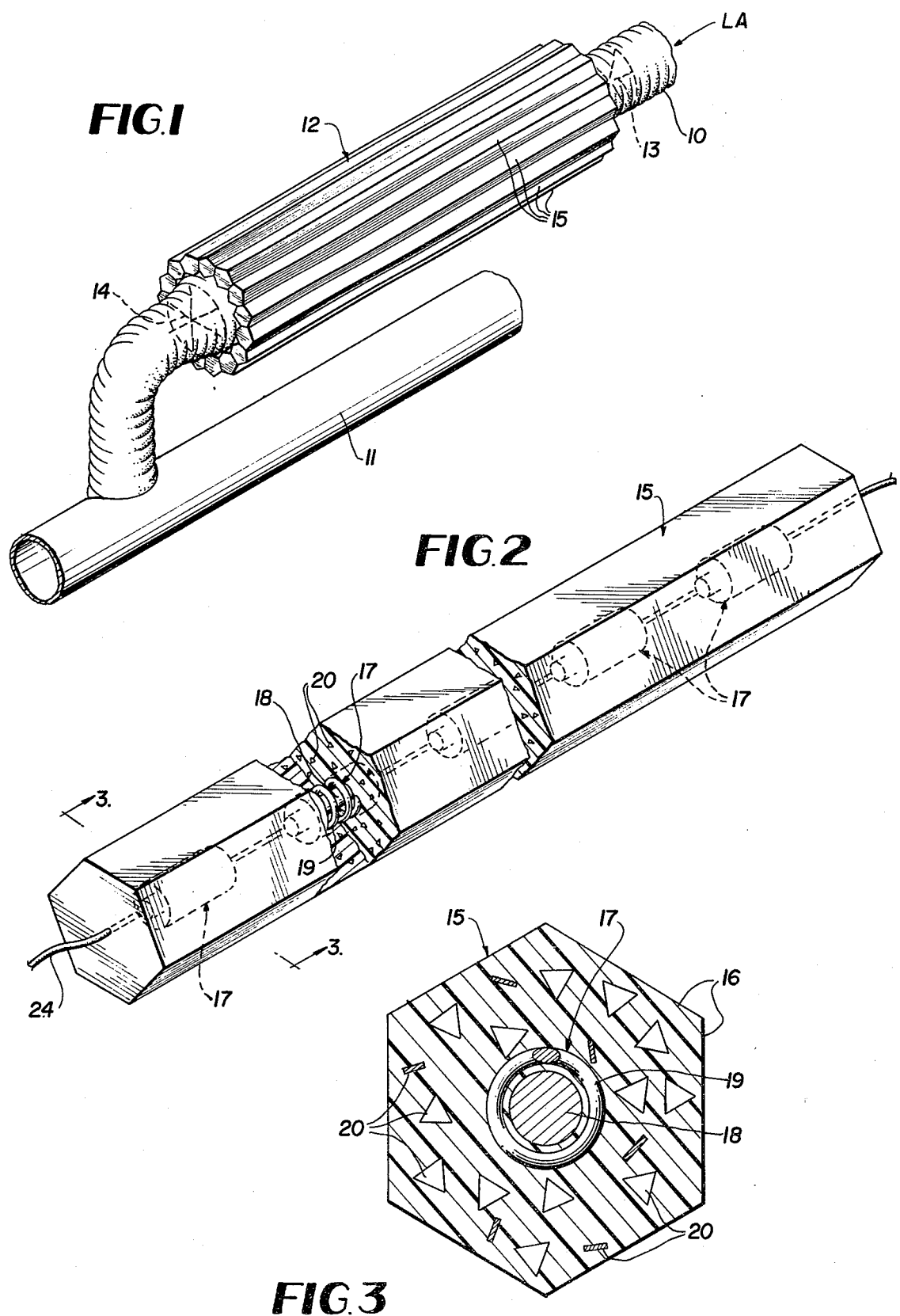

CARDIAC ASSIST DEVICE EMPLOYING ELECTRICALLY STIMULATED ARTIFICIAL MUSCLE

CROSS-REFERENCE TO RELATED APPLICATION

This application contains subject matter in common with copending application Ser. No. 846,109, filed Oct. 27, 1977, for LEFT ATRIAL TO DESCENDING THORACIC AORTA LEFT VENTRICULAR ASSIST DEVICE.

BACKGROUND OF THE INVENTION

As disclosed in the above related application, a thin walled Dacron pouch or conduit is utilized to shunt blood from the left atrium of the heart to the descending throacic aorta in a left ventricular assist device. The device includes a rectangular cross section compression chamber for the Dacron pouch or shunt, the latter being equipped with a pair of Porcine valves near opposite ends of the compression chamber.

Within the compression chamber, a flat rectangular ejection plate is cyclically operated by the action of a connected follower element and a rotationally driven spirally grooved or slitted member connected with the output shaft of an electric motor driven by induction across the intact skin of a recipient of the device. The device of the prior application causes cyclic compression of the Dacron pouch to force predetermined volumes of blood from the left atrium into the descending thoracic aorta.

The present invention dispenses entirely with the rigid compression chamber, the ejection plate and associated mechanical drive means, thus eliminating, to a great extent, the hardware which must be implanted in the body of a recipient of a cardiac assist device of this type. Instead of these elements, the invention utilizes an artifical muscle in the form of a sheath surrounding the Dacron pouch or shunt, and cyclically this muscle sheath is electrically energized or stimulated to cause contraction of the muscle on the flexible shunt so that predetermined amounts of blood from the left atrium are pumped from the shunt into the descending thoracic aorta. The required stimulation and contraction of the artificial muscle sheath is obtained through the invention across the intact skin of the recipient by state of the art induction means which is operable to cyclically energize embedded electromagnets in multiple joined rod-like elastomer segments of the muscle sheath which also have magnetically attractable particles dispersed therethrough.

The construction of the assist device utilizing the artificial muscle in lieu of mechanical pumping means is much simpler and much more compact. The artificial muscle, being of a pliable nature, is more compatible with the portions of the human anatomy which are involved in comparison to the prior art.

While the electrically stimulated artifical muscle sheath is employed herein in a particular form of cardiac assist device, it should be understood that many other applications of the muscle can be visualized. The individual muscle segments can be joined together in sheets, rolls or other configurations and may consist of more than one layer of segments for various uses. Generally speaking, the narrower the individual rod-like segments are made and the more segments per artificial muscle layer, the greater is the degree of muscle contraction which can be obtained. The intensity of simulated muscle contraction is a function of current, the type and size of electromagnets employed, the type of elastic matrix, and the density of the ferromagnetic aggregate dispersed throughout the matrix.

Other features and advantages of the invention will become apparent during the course of the following description.

BRIEF DESCRIPTION OF THE DRAWINGS

FIG. 1 is a fragmentary perspective view of a left ventricular assist device including an artificial muscle sheath embodying the invention.

FIG. 2 is an enlarged fragmentary perspective view of a single segment of the artificial muscle according to the invention.

FIG. 3 is an enlarged transverse vertical section taken on line 3—3 of FIG. 2.

DETAILED DESCRIPTION

Figure 4:
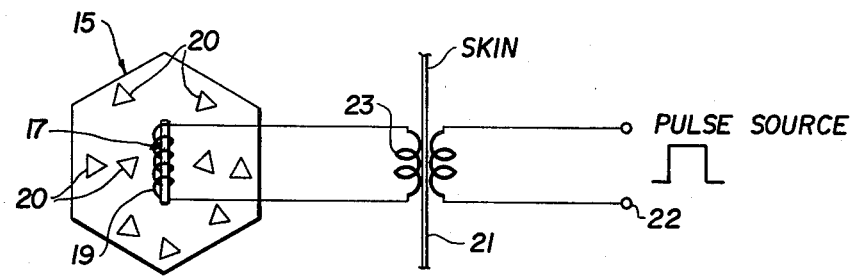
FIGS. 4 and 5 are schematic views showing state of the art electrical stimulating means for the artificial muscle segments in relaxed and contracted states of the latter, respectively.

Referring to the drawings in detail, wherein like numerals designate like parts, the numeral 10 designates a preferably Dacron flexible conduit or pouch forming a shunt from the left atrium, not shown, to the descending thoracic aorta 11, as disclosed in FIG. 1 of the referenced prior application. In lieu of the motorized mechanical compression means in said application for cyclically compressing the shunt 10, the present invention employs an electrically stimulated artificial muscle sheath 12 for this purpose, the muscle sheath forming the main subject matter of the invention. As in the prior application, the Dacron conduit shunt 10 is equipped with a pair of spaced check valves 13 and 14, preferably Porcine valves or other state of the art valves such as Cooley-Cutter disc valves. The artificial muscle sheath can vary in length, and is elongated as shown in FIG. 1, and positioned between the two one-way opening and one-way closing conventional valves 13 and 14.

The artificial muscle sheath 12 is formed from any required number of rod-like elastomer segments 15 which may be hexagonal in cross section, as illustrated, square, cylindrical or other shapes, in some instances. The necessary number of rod-like segments 15 are bonded or fused together on adjacent flat faces 16 to make the unitary tubular sheath 12. Each segment 15 of the artificial muscle is preferably formed of foam rubber, rubber-oid, or some other suitable elastomer.

Embedded within each elastomer segment 15 centrally is a plurality of series connected spaced electromagnets 17 each having a magnetizable core 18 and a surrounding coil 19, as illustrated. The series connected electromagnets 17 are arranged axially within each segment 15 and are molded permanently in place so as to be surrounded by the elastomer matrix forming the rod-like segment 15.

Also embedded within the elastomer matrix of each segment 15 and dispersed throughout the entire length of the segment 15 in randomly spaced relationship is a multitude of minute fragments or chips 20 of magnetically attractable material. Various efficient materials for this purpose are commercially available. For maximum efficiency, the cores 18 of electromagnets 17 are formed of samarium-cobalt. The dispersed magnetically attractable particles 20 in the segments 15 are spaced from one another and spaced from the centrally located electromagnets 17.

The artificial muscle sheath 12 consisting of the required number of joined rod-like elastomer segments 15, as described, is fitted onto the Dacron shunt 10 at the proper location between the valves 13 and 14. When the artificial muscle sheath is in a relaxed or non-stimulated state, FIG. 6, it has a first comparatively large diameter and the Dacron shunt 10 is fully expanded and under essentially no compression from the muscle sheath. When the muscle sheath 12 is electrically stimulated or energized in a manner to be further described, the electromagnets 17 of each segment 15 are all energized and the embedded particles, fragments or chips 20 are magnetically attracted inwardly toward the axial center of the segment 15 by the electromagnets. This action actually reduces the cross sectional area of each elastomer segment 15 in the muscle sheath 12 as graphically illustrated in FIG. 7, in comparison to FIG. 6. Since the adjacent rod-like segments 15 of the muscle sheath 12 are joined, as described, the contraction of the individual segments 15 will collectively cause circumferential contraction of the entire muscle sheath 12, FIG. 7, so that its diameter is substantially reduced during electrical stimulation. This occurs cyclically in the operation of the invention, to cyclically compress the shunt 10 and expel predetermined volumes of blood from the shunt through the valve 14 and into the descending thoracic aorta 11 in substantially the same manner that the mechanical means in the referenced prior application expels or pumps blood as a left ventricle assist means. When the check valve 14 opens during constriction of the shunt 10, the valve 13 will close to prevent back flow of blood toward the left atrium, as in the prior application.

Figure 5:
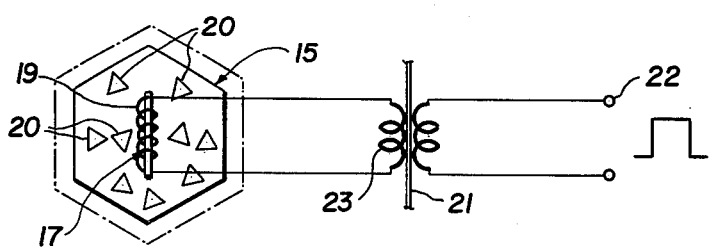
Figure 6:
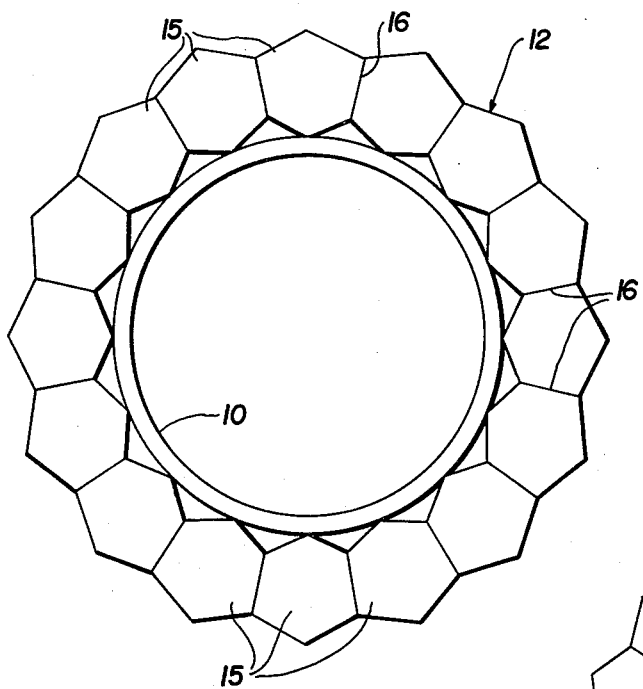
FIGS. 6 and 7 are partly diagrammatic end views of the artificial muscle sheath and left atrial to descending thoracic aorta shunt in a relaxed and contracted state of the muscle sheath, respectively.
Figure 7:
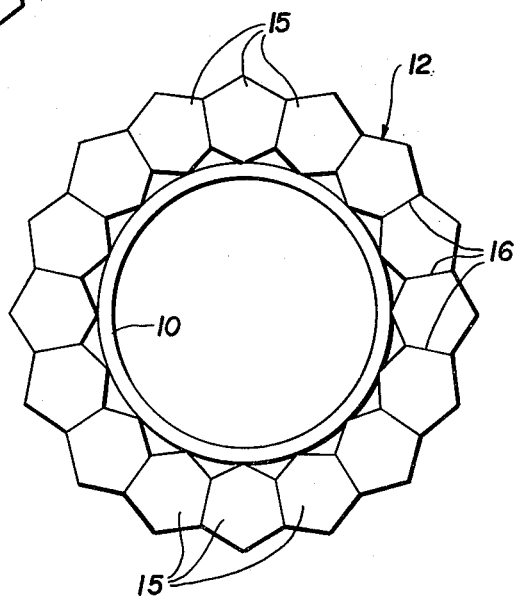

The artificial muscle sheath 12 is electrically energized or stimulated across the intact skin 21 of a recipient without the necessity for any external tether by state of the art means. As illustrated in FIGS. 4 and 5, this means comprises a pulsating source of current 22 to energize a conventional induction means 23 electrically coupled with the series connected coils 19 of the electromagnets 17 in each elastomer segment 15 of the artificial muscle sheath 12. FIG. 4, like FIG. 6, shows the segment 15 relaxed with a comparatively large cross section, while FIG. 5, like FIG. 7, shows the segment contracted by energization of the string of electromagnets 17 therein. The rate of contraction and expansion of the muscle sheath 12 can be controlled and adjusted to provide the required pumping rate by state of the art controls which need not be disclosed herein.

The artificial muscle sheath 12 is compact and efficient and substantially free of all external connections except for the lead wires 24 which connect the electromagnets 17 in series and also connect all of the electromagnets of the muscle sheath into the induction stimulating means 22–23. While a muscle tube or sheath 12 has been described for a particular use or application in forming a cardiac assist device, it can readily be understood that the artificial muscle can have various configurations and can be used in many ways.

It is to be understood that the form of the invention herewith shown and described it to be taken as a preferred example of the same, and that various changes in the shape, size and arrangement of parts may be resorted to, without departing from the spirit of the invention or scope of the subjoined claims.

I claim:

1. A cardiac assist device comprising a tubular shunt adapted for extending from the left atrium to the descending thoracic aorta and having spaced check valves therein, and an artificial muscle sheath formed of an elastomer substantially surrounding said shunt in the region between said check valves, the artificial muscle sheath having magnetically attractable particles dispersed therethrough internally and also having internal electromagnet means adapted to be energized for magnetically attracting said dispersed particles and thereby contracting the artificial muscle sheath around said shunt and expelling blood from the shunt into the descending thoracic aorta.

2. A cardiac assist device as defined in claim 1, and said artificial muscle sheath constructed from a plurality of connected rod-like side-by-side segments each containing a plurality of series connected axially spaced centrally located embedded electromagnets surrounded by said dispersed magnetically attractable particles.

3. A cardiac assist device as defined in claim 2, and said rod-like segments of said sheath having opposing flat interfaces which are joined over substantially their entire areas of contact along the full length of the sheath.

4. A cardiac assist device as defined in claim 3, and said rod-like segments being polygonal in cross section and being substantially uniform in cross sectional area.

5. A cardiac assist device as defined in claim 4, and said segments being hexagonal in cross section.

6. A cardiac assist device as defined in claim 1, and said elastomer comprising a foam rubber-like material.

7. A cardiac assist device as defined in claim 1, and electrical induction means coupled with said electromagnet means and adapted to be energized across the intact skin of a recipient of said device.

8. A cardiac assist device as defined in claim 1, and the electromagnet means comprising a plurality of axially extending series connected circumferentially spaced groups of electromagnets embedded bodily within the elastomeric matrix forming said muscle sheath, and each group of series connected electromagnets being surrounded by a multitude of said dispersed magnetically attractable particles, said particles embedded bodily within said matrix.

9. An artificial muscle comprising an elastomer matrix, electromagnets embedded within said matrix and adapted to be energized by remote induction means coupled with coils of the electromagnets, particles of magnetically attractable material dispersed within said matrix in spaced relationship to one another and to said electromagnets, said artificial muscle elastomer matrix formed of multiple connected rod-like segments in side-by-side relationship, a plurality of series connected axially arranged spaced electromagnets embedded centrally in each rod-like segment, and a multiplicity of said magnetically attractable particles disposed in surrounding relationship to the electromagnets in each rod-like segment.

* * * * *